United States Patent [19]

Perlaky

[11] Patent Number: 5,089,240
[45] Date of Patent: Feb. 18, 1992

[54] CATALYTIC LENS STERILIZING SYSTEM

[75] Inventor: Steven C. Perlaky, Mobile, Ala.

[73] Assignee: Ciba Vision Corporation, Atlanta, Ga.

[21] Appl. No.: 570,900

[22] Filed: Aug. 22, 1990

[51] Int. Cl.$^5$ .............................................. A61L 02/00
[52] U.S. Cl. ..................................... 422/300; 422/301; 422/310; 206/5.1
[58] Field of Search .................. 422/28, 30, 300, 301, 422/305, 310; 206/5.1, 438; 252/106; 424/616; 514/839, 840

[56] References Cited

U.S. PATENT DOCUMENTS

| | | | |
|---|---|---|---|
| 3,912,451 | 10/1975 | Gaglia, Jr. | 422/30 |
| 3,939,968 | 2/1976 | Ryder | 206/5.1 |
| 4,396,583 | 8/1983 | LeBoeuf | 422/30 |
| 4,780,152 | 10/1988 | Itagaki et al. | 422/37 |
| 4,817,988 | 4/1989 | Ryder et al. | 206/5.1 |
| 4,889,693 | 12/1989 | Su et al. | 422/113 |
| 5,011,661 | 4/1991 | Schäfer et al. | 422/30 |

Primary Examiner—Robert J. Warden
Assistant Examiner—Theresa A. Trembley
Attorney, Agent, or Firm—Trexler, Bushnell, Giangiorgi & Blackstone, Ltd.

[57] ABSTRACT

An appliance for sterilizing contact lenses or the like includes a reaction vessel for containing the lenses in sterilizing contact with hydrogen peroxide solution and two catalytic elements for decomposing the hydrogen peroxide during the lens sterilization. The first catalytic element decomposes a portion of the initial concentration of hydrogen peroxide in the solution during the lens sterilization, and the second catalytic element accelerates combined decomposition of the reduced concentration of hydrogen peroxide in the solution resulting from decomposition by the first catalytic element, in order to achieve sufficiently reduced terminal hydrogen peroxide concentration at completion of the lens sterilization for safe contact by the eyes of a wearer with residues of hydrogen peroxide at the terminal concentration which may adhere to the sterilized lenses.

27 Claims, 2 Drawing Sheets

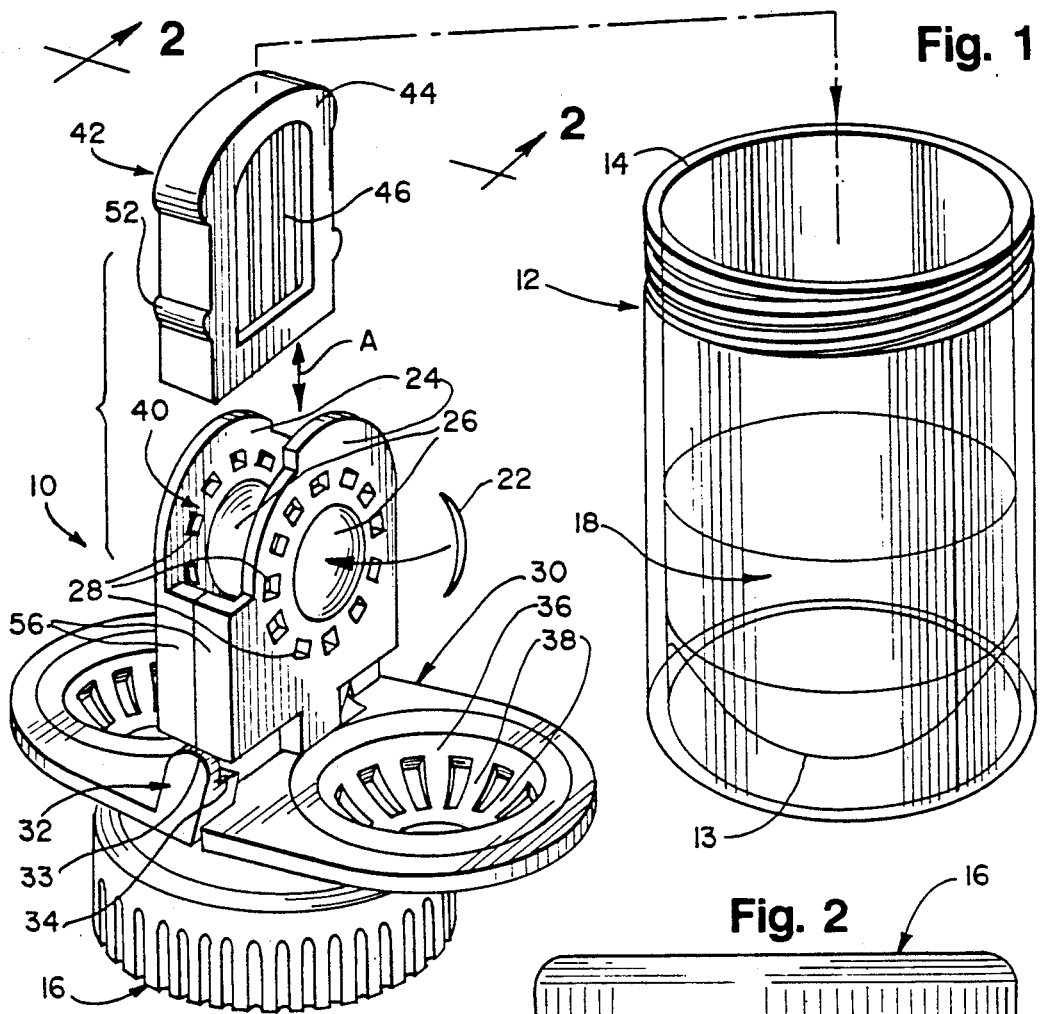
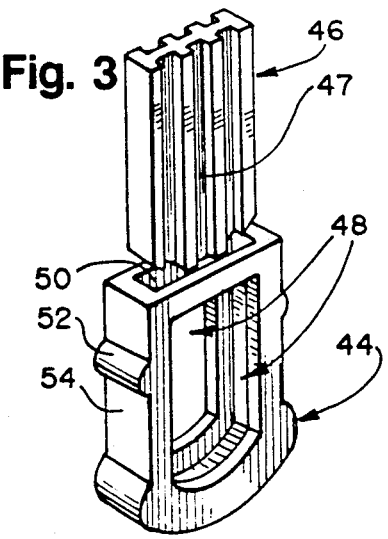
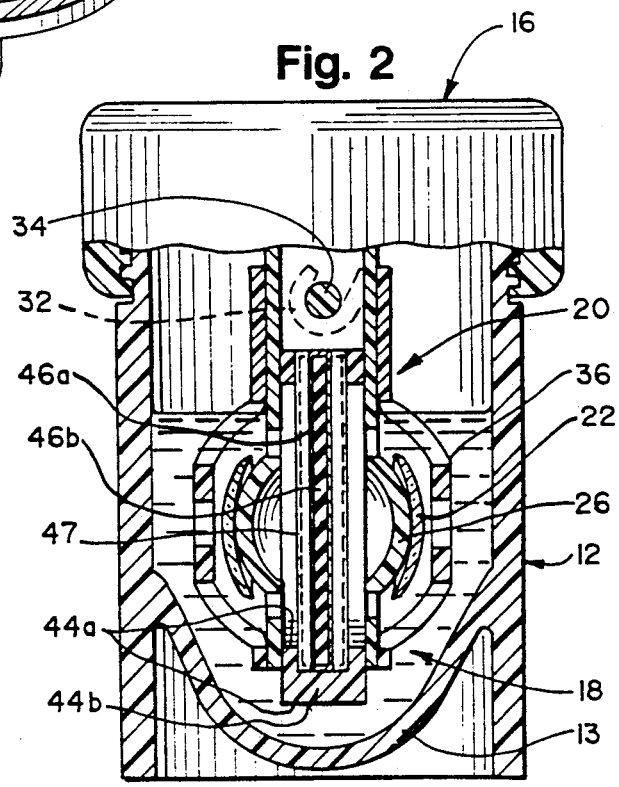
Fig. 1
Fig. 2
Fig. 3

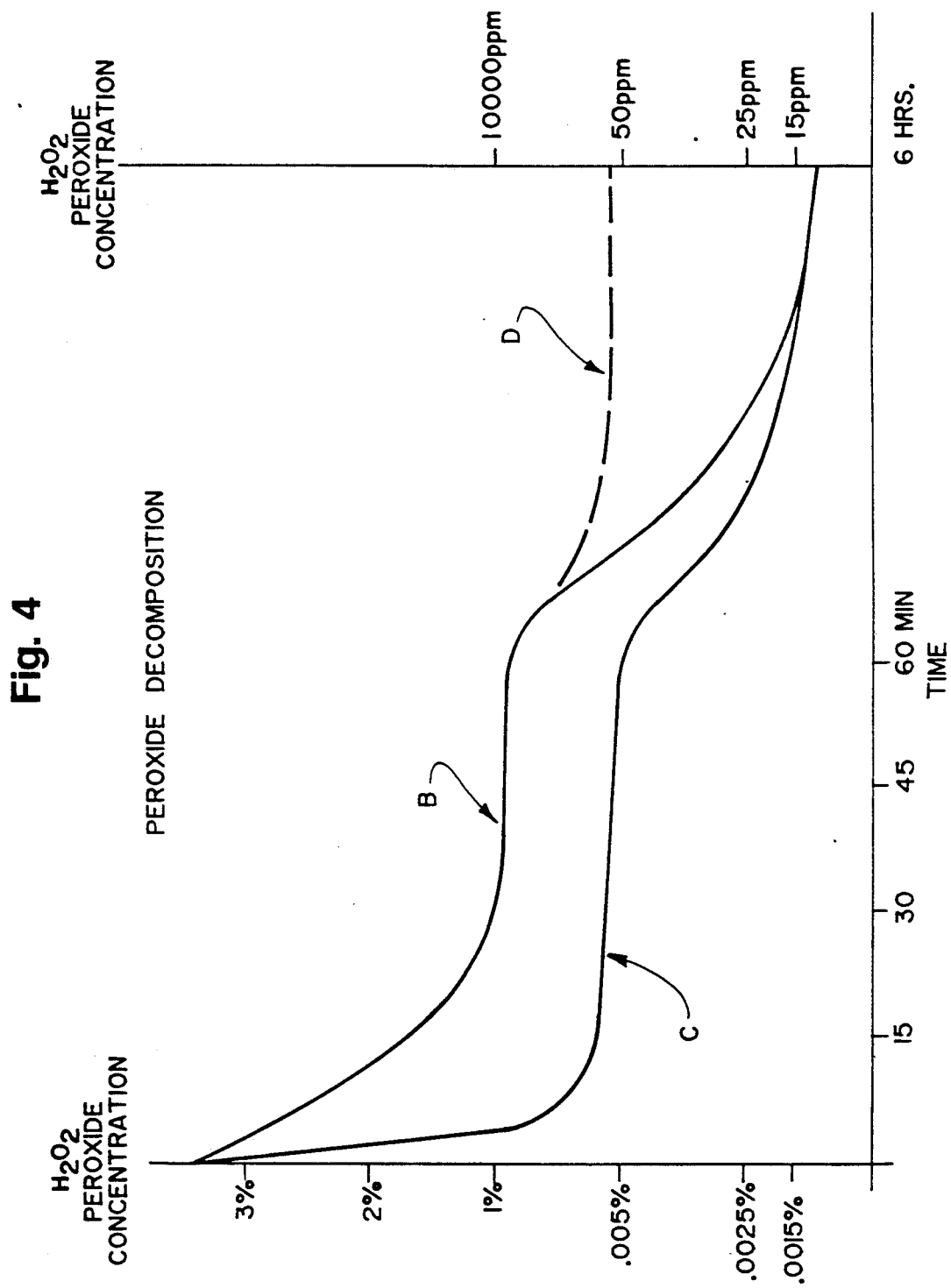

CATALYTIC LENS STERILIZING SYSTEM

BACKGROUND OF THE INVENTION

This invention relates to sterilization of contact lenses using hydrogen peroxide as disinfectant, and more particularly relates to improved catalytic control of the decomposition of hydrogen peroxide in the lens disinfection process.

The well-known, commercialized soft contact lens disinfection process employing hydrogen peroxide solution as a bactericide is described for example in U.S. Pat. Nos. 4,750,610; 4,013,410 and 3,912,451. Recent improvements in contact lens cases for conducting such disinfection process are described in copending U.S. patent application Ser. No. 364,471 filed June 9, 1989 which is incorporated by reference herein. In such process, the contact lenses are immersed overnight in a weak bactericidal solution of hydrogen peroxide which is also subjected to platinum catalyst to promote gradual decomposition of the hydrogen peroxide since significant hydrogen peroxide residues upon contact lenses can cause harm and irritation to the eyes of contact lens wearers. It has generally been recommended not only to allow sufficient time for nearly complete decomposition of the hydrogen peroxide, but additionally to employ a rinsing solution to flush any potential hydrogen peroxide residues from the lenses before insertion into the eyes. One object of the present invention is to improve the catalytic control over the hydrogen peroxide lens disinfection process, while additionally ensuring that upon completion of the lens disinfection process, the terminal hydrogen peroxide concentration is sufficiently reduced for safe contact by residues adhering to the disinfected lenses with the eyes of the wearer.

SUMMARY OF THE INVENTION

In accordance with the present invention, an appliance for sterilizing contact lenses or the like includes a reaction vessel for containing the lenses in sterilizing contact with hydrogen peroxide solution and two catalytic elements for decomposing the hydrogen peroxide during the lens sterilization. The first catalytic element decomposes a portion of the initial concentration of hydrogen peroxide in the solution during the lens sterilization, and the second catalytic element accelerates combined decomposition of the reduce concentration of hydrogen peroxide in the solution resulting from decomposition by the first catalytic element, in order to achieve sufficiently reduced terminal hydrogen peroxide concentration at completion of the lens sterilization for safe contact by the eyes of a wearer with residues of hydrogen peroxide at the terminal concentration which may adhere to the sterilized lenses. The first catalytic element can be a hydrogen peroxide decomposition agent, preferably platinum, disposed on a supporting substrate, for example a thermoplastic polymer alloy of components including bisphenol A polycarbonate, styrene and acrylonitrile copolymer, and ABS. The second catalytic element can be a hydrogen peroxide decomposition agent, preferably platinum, disposed on a supporting substrate, for example, an elastomeric composition.

In a preferred embodiment, the first and second catalytic elements are joined to form a composite catalytic unit which is removably secured on the supporting structure which holds a pair of contact lenses so that the catalytic unit is inserted into the hydrogen peroxide solution at the same time the lenses are first immersed in the solution, to prevent any premature initiation of the catalytic hydrogen peroxide decomposition. In the composite catalytic unit, the first catalytic element forms a frame structure into which the second catalytic element is inserted so that the opposite lateral surfaces of the second catalytic element insert are exposed through openings in the frame structure.

BRIEF DESCRIPTION OF THE DRAWINGS

FIG. 1 is a partially exploded perspective view of one embodiment of a sterilization appliance in accordance with the present invention;

FIG. 2 is a sectional view of the appliance shown in FIG. 1 illustrating use during sterilization;

FIG. 3 is an exploded view of a composite catalytic unit as shown in FIG. 1; and FIG. 4 is a graphical comparison illustrating the hydrogen peroxide decomposition performance of a composite catalyst system in accordance with the present invention relative to performance of a conventional catalyst.

DESCRIPTION OF THE ILLUSTRATED EMBODIMENT

Referring to FIG. 1, a sterilizing appliance in accordance with the present invention is designated generally by reference numeral 10. Appliance 10 includes a generally cylindrical reaction vessel 12 which has an open top 14. The top 14 is threaded to accept a threaded cap member 16. The reaction vessel 12 is designed to contain a contact lens sterilizing solution of aqueous hydrogen peroxide 18. The conventional solution 18 is approximately 3% hydrogen peroxide buffered for sterilization of typical soft contact lenses. The initial concentration of the hydrogen peroxide solution can be varied to suit the sterilization application and decomposition catalyst as more fully described hereinafter.

Depending and welded into the cap 16 is a lens support structure generally designated by reference numeral 20 which projects downwardly into the container 12 to immerse a pair of lenses 22 in the sterilization solution 18 when the cap 16 is mounted thereon as shown in sectional view of FIG. 2. The support structure 20 includes a pair of opposing frame members 24, 24 each having respective lens receiving surface 26 adapted to accept the concave surface of the lens 22. The surface 26 is surrounded by an annular pattern of perforations 28 through the respective frame members 24 which allow passage of the hydrogen peroxide solution 18 as well as oxygen bubbles. The support structure 20 also includes a pair of opposingly pivotal lens holder cover members 30 having arms 32 which are pivotally supported on opposing bearing pins 34 so that each of the lens holder cover members 30 pivotally swings independently. Each of the lens holder cover members 30 includes an apertured, dome-shaped lens cover 36 formed as a series of spaced spokes 38. When the lens cover 36 is pivoted to a fully closed position to enclose the lens 22 upon the support surface 26, the sterilizing solution 18 passes between the spoke 38 to immerse the lens 22. The end 33 on each of the respective pivot arms 32 enables a snap-open and snap-shut interference fit against the respective frame member 24 in order to retain the pivotally closed position of the holder and cover members 30.

The frame members 24 are spaced to form an open-ended central cavity 40 which receives a composite catalyst unit 42 removably inserted therein as indicated by arrow A. The catalyst unit 42 includes a first catalytic element 44 which is fabricated to provide a generally surrounding frame which supports the second catalytic element insert 46 therein. The frame structure of the element 44 provides large side openings 48 to enable extensive exposure of the lateral surfaces of the second catalytic element insert 46 with ribs 47 to the hydrogen peroxide solution 18 as discussed further hereinafter. The second catalytic element 46 is frictionally installed within the first catalytic frame 44 through an end aperture 50 as shown in FIG. 3. The frame 44 has a pair of lug teeth 52 projecting from the lateral surfaces 54 so that the lugs 52 frictionally engage the end surfaces 56 of the frame members 24 to removably retain the catalytic unit 42 within the cavity 40 as best shown in FIG. 2. Since the catalytic unit 42 is secured on the lens support structure 20 the catalytic unit 42 is inserted into the hydrogen peroxide solution 18 at the same time the lenses 22 are first immersed therein so that the catalytic decomposition of the hydrogen peroxide is not prematurely initiated. The rounded interior bottom wall 13 of the container 12 prevents excessive diffusion path length for hydrogen peroxide molecules migrating to the centrally positioned catalyst unit 42 from the bottom strata of solution 18. Additionally, the catalytic unit 42 remains secured to the support structure 20 and the cap 16 without the need for manipulation by the user during successive sterilization procedures, but the catalyst unit 42 is easily removed and replaced when it has become deactivated.

Broadly, the first catalytic element which in the illustrated embodiment forms the frame 44 functions to decompose the hydrogen peroxide in the initial concentration of the solution 18 which is charged into the container 12 at the beginning of the lens sterilization procedure. The second catalytic element functions to accelerate the decomposition of the hydrogen peroxide in the reduced concentration of the solution 18 resulting from the decomposition of the hydrogen peroxide at the initial, higher concentration achieved under the catalytic action of the first catalytic element 44. The catalytic action of the insert 46 achieves sufficiently reduced terminal hydrogen peroxide concentration at completion of the lens sterilization procedure, for safe contact by the eyes of the wearer with residues of hydrogen peroxide at the terminal concentration which may adhere to the sterilized contact lenses. In the conventional contact lens sterilization with the typical buffered solution of hydrogen peroxide at a concentration of approximately 3%, the commercially employed platinum catalyst supported on molded Noryl ® (as more fully described in the aforementioned U.S. Patents) produces rapid hydrogen peroxide decomposition to a concentration below 0.5% in approximately 6 minutes or less; in contrast, one objective for the first catalytic element in accordance with the present invention is to comparatively retard the hydrogen peroxide decomposition rate so as to maintain the hydrogen peroxide concentration above approximately 1% for at least 30 minutes in order to improve assurance of adequate contact lens sterilization, and the second catalytic element ensures the continued hydrogen peroxide decomposition at the resulting lower concentrations will continue so that the safe terminal hydrogen peroxide concentration for eye contact will be achieved in no more 6 hours to completion of the sterilization procedure to allow the wearers reuse of the lenses.

The primary hydrogen peroxide decomposition performance of the second catalytic element primarily at the lower hydrogen peroxide concentrations, for example 300 ppm, is generally promoted by large active surface area of the second catalytic element, further increased by ribs 47, for exposure to the dilute hydrogen peroxide concentrations, whereas the first catalytic element is more active at the higher initial concentrations, typically 3%.

In the present invention, suitable hydrogen peroxide decomposition catalysts include metals from Periods 4, 5 and 6 of the Periodic Chart of Elements and the lanthanide elements which are disposed on a carrier or substrate to extend the active surface area of the catalytic metal. Among the metal hydrogen peroxide decomposition catalysts belonging to the aforementioned Periods 4, 5 and 6, are, for example, Pt, Pd, Ir, Rh, Re, Au, Ag, Cu, Cr, Os, Co, Fe, Mo, W, Mn, Ce and Th.

Particularly for commercial reasons, platinum is the preferred hydrogen decomposition catalytic metal in accordance with the present invention. Preferably, the platinum is disposed on an inexpensive support material which can be fabricated to provide a resulting catalytic element with extensive active surface area. As best shown in the embodiment of FIG. 2, the frame 44 of the first catalytic element includes the catalytically active coating 44a supported on the molded substrate 44b. Particularly suitable materials for the substrate support include polymeric materials which are not only inexpensive but can be inexpensively molded and on which the catalytic platinum can be securely disposed. Thus, in the illustrated embodiment, the frame 44 of the first catalytic element is preferably defined by a substrate support 44b molded from polymeric material. Particularly good catalytic performance in comparatively retarding the hydrogen peroxide decomposition has been obtained by depositing platinum metal on a polymeric substrate having a composition comprising thermoplastic polymer alloy including an elastomeric component; exemplary of such materials is a thermoplastic alloy of components including bisphenol A polycarbonate, styrene and acrylonitrile copolymer (SAN) and ABS, such as the commercial polymeric molding material marketed under the trademark Bayblend ™ by Mobay Corporation in a particularly preferred grade designated T-84. The platinum metal can be deposited on the polymeric alloy substrate using metal deposition techniques such as chemical deposition, vapor deposition, vacuum metalization, electroplating, or sputtering as more fully described in the aforementioned U.S. Pat. No. 3,912,451. Platinum deposition according to the commercially practiced process employed by Johnson-Mathey Company produced excellent platinum deposition on polymeric alloys molded to enable a first catalytic element in the configuration of the frame 44.

The second catalytic element 46 can be fabricated from any of the hydrogen peroxide decomposition metals as the first catalytic element, particularly platinum, however the platinum is preferably deposited on a substrate support which preferably contributes a surface morphology tending to retard the activity of the platinum in decomposing hydrogen peroxide at the higher initial 3% concentration but is more effective decomposing lower concentration of hydrogen peroxide. As best shown in the embodiment of FIG. 2, the insert 46 of the second catalytic element includes the catalytically active coating 46a supported on the molded substrate 46b.

Very effective performance of lower concentration hydrogen peroxide decomposition by the second catalytic element has been obtained by depositing platinum on a support substrate having a primarily elastomeric composition. Suitable elastomeric compositions include elastomeric alloys including thermoplastic rubbers commercially available under the trademark Santoprene ® from Monsanto Company. Particularly good performance of a second catalytic element has been obtained with platinum deposited on Santoprene ® in a grade designated 271-64 which was effective in completing the decomposition of hydrogen peroxide in reduced concentrations to achieve safe residual hydrogen peroxide concentration in residues, without significantly accelerating the decomposition of the initial hydrogen peroxide concentration in the charged solution.

The following examples are illustrative of embodiments in accordance with the present invention but do not indicate limitation upon the scope of the claims.

EXAMPLE 1

A substrate support for the frame 44 of the first catalytic element was injection molded approximately 1" square from Bayblend T-84 thermoplastic polymer alloy using a hand loaded core to produce the through openings 48 and aperture 50. The frame was coated with platinum from chloroplatinic acid employing the deposition procedure of Johnson-Mathey Co.

EXAMPLE 2

A substrate support for the second catalytic element insert 46 for installation within the frame 44, was molded from Santoprene ® 271-64 thermoplastic rubber and then coated with platinum using the Johnson-Mathey procedure as in Example 1.

EXAMPLE 3

The platinum coated Santoprene ® prepared according to Example 2 was installed within the platinum coated frame prepared according to Example 1 to provided a composite catalyst unit 42 as illustrated in FIGS. 1 and 3. The composite catalyst unit 42 was then evaluated for hydrogen peroxide decomposition during sterilization of a pair of contact lenses 22 using a conventional 3% hydrogen peroxide buffered solution in an appliance 10 equipped with an oxygen venting structure (not shown) as described in U.S. Pat. No. 4,956,156. The hydrogen peroxide decomposition performance curve is indicated by reference letter B in FIG. 4 which illustrates that the hydrogen peroxide concentration is maintained at or above 1% for approximately 30 minutes but is subsequently reduced to the non-eye irritant level less than 15 ppm within 6 hours. In contrast, the performance curve indicated by reference letter C illustrates the conventional catalytic element and configuration as described for example in the aforementioned U.S. Pat. No. 4,750,610. By comparison, the conventional catalyst produces decomposition of the hydrogen peroxide to a concentration below 0.5% typically in less than 6 minutes.

EXAMPLE 4

For comparative demonstration, a single catalytic element was injection molded from Bayblend T-84 alloy and then platinum coated as described in Example 1. The single catalytic element was then evaluated for hydrogen peroxide decomposition performance using a lens sterilization appliance and procedure as described in Example 3. The resulting performance curve of this single catalytic element was identical to the curve B in FIG. 4 for the composite catalyst unit until a time of about 80-90 minutes, after which the single catalyst curve indicated at D began to flatten to a time-independent level of approximately 100 ppm hydrogen peroxide, relative to the continued reduction to a level below 15 ppm hydrogen peroxide after 6 hours produced by the composite catalyst unit illustrated by curve B.

While particular embodiments of the present invention have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

The invention is claimed as follows:

1. An appliance for use in sterilizing contact lenses, comprising:
   a) a reaction vessel for containing contact lenses in sterilizing contact with hydrogen peroxide solution;
   b) a first catalytic element for decomposing a portion of an initial concentration of a hydrogen peroxide solution during said lens sterilization;
   c) a second catalytic element effective for comparatively accelerating decomposition, relative to said first catalytic element, of the reduced concentration of hydrogen peroxide in said solution resulting from said partial decomposition of said initial hydrogen peroxide concentration, in order to achieve sufficiently reduced terminal hydrogen peroxide concentration at completion of said sterilization, for safe contact by the eyes of a wearer with residues of hydrogen peroxide at said terminal concentration adhering to said sterilized contact lenses.

2. An appliance according to claim 1, wherein said first and second catalytic elements are joined to form a composite catalytic unit.

3. An appliance according to claim 1, wherein said first catalytic element comprises a hydrogen peroxide decomposition agent disposed on a supporting substrate.

4. An appliance according to claim 1, wherein said first catalytic element comprises a hydrogen peroxide decomposition metal deposited on a supporting substrate.

5. An appliance according to claim 1, wherein said first catalytic element comprises platinum deposited on a polymeric substrate.

6. An appliance according to claim 5, wherein said polymeric substrate has a composition comprising an elastomeric component.

7. An appliance according to claim 5, wherein said polymeric substrate has a composition comprising thermoplastic polymer alloy.

8. An appliance according to claim 1, wherein said polymeric substrate has a composition comprising ABS.

9. An appliance according to claim 5, wherein said polymeric substrate has a composition comprising bisphenol A polycarbonate.

10. An appliance according to claim 5, wherein said polymeric substrate has a composition comprising a thermoplastic alloy of components including bisphenol A polycarbonate, styrene and acrylonitrile copolymer, and ABS.

11. An appliance for use in sterilizing contact lenses, comprising:
   a) a reaction vessel for containing contact lenses in sterilizing contact with hydrogen peroxide solution;
   b) a first catalytic element for decomposing a portion of an initial concentration of a hydrogen peroxide solution during lens sterilization, wherein the catalytic activity of said first catalytic element controls decomposition of an approximately 3% initial concentration of hydrogen peroxide in said solution to maintain at least 1% concentration of hydrogen peroxide in the solution for at least 30 minutes after initial contact of said first catalytic element with said 3% hydrogen peroxide solution;
   c) a second catalytic element effective for comparatively accelerating decomposition, relative to said first catalytic element, of the reduced concentration of hydrogen peroxide in said solution resulting from said partial decomposition of said initial hydrogen peroxide concentration, in order to achieve sufficiently reduced terminal hydrogen peroxide concentration at completion of said sterilization, for safe contact by the eyes of a wearer with residues of hydrogen peroxide at said terminal concentration adhering to said sterilized contact lenses.

12. An appliance according to claim 1, wherein said second catalytic element comprises a hydrogen peroxide decomposition agent disposed on a supporting substrate.

13. An appliance according to claim 12, wherein said second catalytic element comprises a hydrogen peroxide decomposition metal deposited on a supporting substrate.

14. An appliance according to claim 12, wherein said second catalytic element comprises platinum deposited on a polymeric substrate.

15. An appliance according to claim 14, wherein said polymeric substrate has a composition comprising elastomer.

16. An appliance according to claim 1, wherein said first catalytic element comprises a frame structure into which said second catalytic element is inserted for exposure therewithin to said hydrogen peroxide solution.

17. An appliance for use in sterilizing contact lenses, comprising:
   a) a reaction vessel for containing contact lenses in sterilizing contact with hydrogen peroxide solution;
   b) a first catalytic element for decomposing a portion of an initial concentration of a hydrogen peroxide solution during lens sterilization;
   c) a second catalytic element effective for comparatively accelerating decomposition, relative to said first catalytic element, of the reduced concentration of hydrogen peroxide in said solution resulting from said partial decomposition of said initial hydrogen peroxide concentration, in order to achieve sufficiently reduced terminal hydrogen peroxide concentration at completion of said sterilization, for safe contact by the eyes of a wearer with residues of hydrogen peroxide at said terminal concentration adhering to said sterilized contact lenses, wherein said first catalytic element comprises a frame structure into which said second catalytic element is inserted for exposure therewithin to said hydrogen peroxide solution and wherein said frame structure includes a through aperture for exposure of oppositely arranged lateral surfaces formed on said inserted second catalytic element.

18. An appliance for use in sterilizing contact lenses, comprising:
   a) a reaction vessel for containing contact lenses in sterilizing contact with hydrogen peroxide solution;
   b) a first catalytic element for decomposing a portion of an initial concentration of a hydrogen peroxide solution during lens sterilization;
   c) a second catalytic element effective for comparatively accelerating decomposition, relative to said first catalytic element, of the reduced concentration of hydrogen peroxide in said solution resulting from said partial decomposition of said initial hydrogen peroxide concentration, in order to achieve sufficiently reduced terminal hydrogen peroxide concentration at completion of said sterilization, for safe contact by the eyes of a wearer with residues of hydrogen peroxide at said terminal concentration adhering to said sterilized contact lenses, wherein said first catalytic element comprises a frame structure into which said second catalytic element is inserted for exposure therewithin to said hydrogen peroxide solution and wherein said frame structure includes an end aperture through which said catalytic element is inserted to form a composition catalytic unit.

19. An appliance according to claim 1, wherein said reaction vessel includes a closed end having an arcuate interior surface for containing said solution.

20. A composite catalytic unit for use in sterilizing contact lenses within a reaction vessel containing hydrogen peroxide sterilization solution, comprising:
   (a) a first catalytic element for decomposing a portion of an initial concentration of said hydrogen peroxide solution during said lens sterilization; and
   (b) a second catalytic element effective for comparatively accelerating decomposition, relative to said first catalytic element, of the reduced concentration of hydrogen peroxide in said solution resulting from said decomposition of said portion of said initial hydrogen peroxide concentration, wherein said first and second catalytic elements are secured together.

21. A composite catalytic unit according to claim 20, wherein said first catalytic element has a configuration defined by a frame structure into which said second catalytic element is inserted.

22. A composite catalytic unit for use in sterilizing contact lenses within a reaction vessel containing hydrogen peroxide sterilization solution, comprising:
   (a) a first catalytic element for decomposing a portion of an initial concentration of a hydrogen peroxide solution during lens sterilization; and
   (b) a second catalytic element effective for comparatively accelerating decomposition, relative to said first catalytic element, of the reduced concentration of hydrogen peroxide in said solution resulting from said decomposition of said portion of said initial hydrogen peroxide concentration, wherein said first and second catalytic elements are secured together, wherein said first catalytic element has a configuration defined by a frame structure into which said second catalytic element is inserted, and said frame structure includes a through opening for exposure of oppositely arranged lateral surfaces formed on said second catalytic element.

23. A composite catalytic unit for use in sterilizing contact lenses within a reaction vessel containing hydrogen peroxide sterilization solution, comprising:

(a) a first catalytic element for decomposing a portion of an initial concentration of a hydrogen peroxide solution during said lens sterilization; wherein the catalytic activity of first catalytic element is effective to control decomposition of an approximately 3% initial concentration of hydrogen peroxide in said solution to maintain at least 1% concentration of hydrogen peroxide in the solution for at least 30 minutes after initial contact of said first catalytic element with said 3% hydrogen peroxide solution; and (b) a second catalytic element effective for comparatively accelerating decomposition, relative to said first catalytic element, of the reduced concentration of hydrogen peroxide in said solution resulting from said decomposition of said portion of said initial hydrogen peroxide concentration, wherein said first and second catalytic elements are secured together.

24. A unitary support structure for holding a pair of contact lenses as well as supporting a composite catalytic unit, for use in sterilizing the contact lenses within a reaction vessel containing hydrogen peroxide sterilization solution, comprising:

(a) a first support means for removably holding a pair of contact lenses; and (b) a second support means removably securing a composite catalytic unit comprising:

(1) a first catalytic element for decomposing a portion of an initial concentration of a hydrogen peroxide solution during said lens sterilization; and (2) a second catalytic element for comparatively accelerating decomposition, relative to said first catalytic element, of the reduced concentration of hydrogen peroxide in said solution, in order to achieve sufficiently reduced terminal hydrogen peroxide concentration at completion of said sterilization for safe contact by the eyes of a wearer with residues of hydrogen peroxide from said terminal concentration adhering to said sterilized contact lenses.

25. A support structure according to claim 24, wherein said first catalytic element comprises a frame structure into which said second catalytic element is inserted for exposure therewithin to said hydrogen peroxide solution.

26. A unitary support structure for holding a pair of contact lenses as well as supporting a composite catalytic unit, for use in sterilizing the contact lenses within a reaction vessel containing hydrogen peroxide sterilization solution, comprising:

(a) a first support means for removably holding a pair of contact lenses;

(b) a second support means for removably securing a composite catalytic unit comprising:

(1) a first catalytic element for decomposing a portion of an initial concentration of a hydrogen peroxide solution during said lens sterilization; and (2) a second catalytic element for comparatively accelerating decomposition, relative to said first catalytic element, of the reduced concentration of hydrogen peroxide in said solution, in order to achieve sufficiently reduced terminal hydrogen peroxide concentration at completion of said sterilization for safe contact by the eyes of a wearer with residues of hydrogen peroxide from said terminal concentration adhering to said sterilized contact lenses;

wherein said first support means holds said respective contact lenses in spaced relationship and said second support means secures said composite catalytic unit between said spaced contact lenses.

27. A support structure according to claim 24, wherein the catalytic activity of said first catalytic element is effective to control decomposition of an approximately 3% initial concentration of hydrogen peroxide in said solution to maintain at least 1% concentration of hydrogen peroxide in the solution for at least 30 minutes after initial contact of said first catalytic element with said 3% hydrogen peroxide solution.

* * * * *